US006573416B1

(12) United States Patent
Randolph

(10) Patent No.: US 6,573,416 B1
(45) Date of Patent: Jun. 3, 2003

(54) HYDROCARBON DISPROPORTIONATION

(75) Inventor: Bruce B. Randolph, Bartlesville, OK (US)

(73) Assignee: ConocoPhillips Company, Houston, TX (US)

( * ) Notice: Subject to any disclaimer, the term of this patent is extended or adjusted under 35 U.S.C. 154(b) by 0 days.

(21) Appl. No.: 09/444,426

(22) Filed: Nov. 19, 1999

(51) Int. Cl.$^7$ ............................... C07C 6/08; C07C 6/10
(52) U.S. Cl. ...................................... 585/708
(58) Field of Search ......................... 585/708

(56) References Cited

U.S. PATENT DOCUMENTS

| | | | | | |
|---|---|---|---|---|---|
| 2,405,996 | A | * | 8/1946 | Burk | 208/114 |
| 2,691,688 | A | * | 10/1954 | Schneider | 585/708 |
| 3,239,577 | A | * | 3/1966 | Bloch et al. | 585/708 |
| 3,679,771 | A | * | 7/1972 | Hutson, Jr. et al. | 585/314 |
| 3,763,032 | A | | 10/1973 | Banks | 208/93 |
| 3,767,565 | A | | 10/1973 | Banks | 208/93 |
| 3,773,845 | A | * | 11/1973 | Hughes | 585/708 |
| 3,775,505 | A | * | 11/1973 | Hughes | 585/708 |
| 5,414,184 | A | * | 5/1995 | Wu et al. | 585/708 |
| 5,489,727 | A | | 2/1996 | Randolph et al. | 585/702 |
| 5,900,522 | A | * | 5/1999 | Hommeltoft | 585/708 |

\* cited by examiner

*Primary Examiner*—Walter D. Griffin
(74) *Attorney, Agent, or Firm*—Jeffrey R. Anderson

(57) ABSTRACT

A process for disproportionating isoparaffins and paraffins in the presence of at least one initiator is disclosed. The product from the disproportionation contains a gasoline range material having a higher octane-rating than the isoparaffins and paraffins in the feed and a diesel range material having a higher cetane number than the isoparaffins and paraffins in the feed.

42 Claims, No Drawings

HYDROCARBON DISPROPORTIONATION

BACKGROUND OF THE INVENTION

The present invention relates to the field of hydrocarbon upgrading processes. In another aspect, the invention relates to the disproportionation of isoparaffinic hydrocarbons.

Disproportionation of hydrocarbons, as referred to herein, involves the conversion of hydrocarbons having x number of carbon atoms per molecule to hydrocarbons having x−1 number of carbon atoms per molecule and to hydrocarbons having x+1 number of carbon atoms per molecule. The production of high octane-rating gasoline is desirable in order to meet the octane specifications for gasoline fuel. One way in which high octane gasoline can be produced is by the disproportionation of hydrocarbons to produce higher octane-rating gasoline, as described in U.S. Pat. Nos. 3,763,032 and 3,767,565. However, as gasoline fuel specifications become more stringent concerning sulfur content, aromatic content and Reid vapor pressure ("RVP", defined as the vapor pressure of a hydrocarbon at 100° F. (37.8° C.) in pounds per square inch absolute and measured using ASTM test method D-323), the demand for diesel fuel could significantly increase should the motor vehicle industry increase the production of motor vehicles running on diesel fuel. Therefore, development of a process to convert a hydrocarbon feedstock comprising gasoline range hydrocarbons, containing paraffins and isoparaffins, to a gasoline range stream with enhanced octane-rating over that of the hydrocarbon feedstock and to a diesel range material having an enhanced cetane number over that of the hydrocarbon feedstock would be a significant contribution to the art and to the economy.

SUMMARY OF THE INVENTION

It is an object of the present invention to provide a novel process for disproportionating isoparaffins and paraffins to produce diesel fuel range hydrocarbons.

It is still another object of the present invention to provide a novel process for disproportionating isoparaffins and paraffins to produce gasoline range hydrocarbons.

It is yet another object of the present invention to provide a novel process for disproportionating isoparaffins and paraffins to produce diesel fuel range hydrocarbons having a higher cetane number than the isoparaffins and paraffins and gasoline range hydrocarbons having a higher octane-rating than the isoparaffins and paraffins.

In accordance with the present invention, a process has been found for disproportionating hydrocarbons comprising the steps of:

contacting a hydrocarbon feedstock comprising isoparaffins and paraffins with a disproportionation catalyst, in the presence of at least one initiator, to thereby produce a product stream comprising a diesel range material; and recovering the diesel range material from the product stream.

In one embodiment, the cetane number of the diesel range material is higher than the cetane number of the hydrocarbon feedstock.

In another embodiment, at least a portion of a hydrocarbon feedstock comprising isoparaffins and paraffins is converted to a gasoline range material and a diesel range material in a process comprising the steps of:

contacting the hydrocarbon feedstock with a disproportionation catalyst, in the presence of at least one initiator, to thereby produce the gasoline range material and the diesel range material having a higher cetane number than the hydrocarbon feedstock, wherein the combined volume of the gasoline range material produced and the diesel range material produced is greater than the volume of the hydrocarbon feedstock;

recovering the gasoline range material; and recovering the diesel range material.

In still another embodiment, the octane-rating of the gasoline range material is higher than the octane-rating of the hydrocarbon feedstock.

Other objects and advantages will become apparent from the detailed description and the appended claims.

DETAILED DESCRIPTION OF THE INVENTION

The catalyst useful in the present invention can be any disproportionation catalyst suitable for disproportionating isoparaffins and paraffins. Preferably, the disproportionation catalyst is acidic, and most preferably, is an acid catalyst. Examples of suitable acid catalysts include, but are not limited to, hydrofluoric acid; sulfuric acid; polyfluoroalkyl sulfonic acids, either neat or supported on a solid; perfluoroalkyl sulfonic acids, either neat or supported on a solid; inorganic metal fluorides (such as, for example boron trifluoride) in the presence of hydrofluoric acid; zeolites (such as, for example MCM-36); alumina; aluminosilicates; and zirconia-based solid acids (such as sulfated or tungstated zirconia). The most preferred acid catalyst useful as the disproportionation catalyst is hydrofluoric acid.

The process of this invention involves disproportionating isoparaffins and paraffins. A hydrocarbon feedstock comprising, consisting essentially of, or consisting of isoparaffins and paraffins is introduced or charged, in the presence of at least one initiator, to a reaction zone containing a disproportionation catalyst operated under reaction conditions for disproportionating isoparaffins and paraffins.

Preferably, the hydrocarbon feedstock comprises isoparaffins and paraffins having the formula $C_nH_{2n+2}$ wherein n is an integer greater than 3; preferably greater than 4; and most preferably greater than 8 (that is, the hydrocarbon feedstock most preferably comprises isoparaffins and paraffins, each having greater than 8 carbon atoms per molecule). In addition, the hydrocarbon feedstock can be an alkylation product from an alkylation unit or the heavy alkylate portion of the alkylate product, the heavy alkylate portion comprising primarily $C_9+$ hydrocarbons.

The at least one initiator can be any initiator effective at initiating the disproportionation of isoparaffins and paraffins. More particularly, the initiator useful in the present invention can be selected from the group consisting of at least one olefin, at least one compound of the formula $C_nH_{2n+1}X$, wherein n is an integer and wherein X is a leaving group capable of leaving under disproportionation conditions to form a carbocation intermediate, and combinations of any two or more thereof.

The at least one olefin of the at least one initiator can be selected from the group consisting of ethylene, propylene, butylene, pentene, isopentene and combinations of any two or more thereof.

The X in the compound can be selected from the group consisting of fluorine, chlorine, bromine, iodine, hydroxide ion, and combinations of any two or more thereof The most preferred initiator is an olefin.

The weight ratio of the hydrocarbon feedstock to the at least one initiator can be any ratio effective for disproportionating the hydrocarbon feedstock. Preferably, the weight ratio of the hydrocarbon feedstock to the at least one initiator is in the range of from about 1:1 to about 100,000:1; more preferably from about 10:1 to about 1,000:1; and most preferably from 20:1 to 100:1.

The disproportionation reaction can take place as a batch process step or, preferably, as a continuous process step. In the latter operation, a solid catalyst bed or a moving catalyst bed or a fluidized catalyst bed or a continuous stirred tank reactor can be employed. Any of these operational modes have advantages and disadvantages, and those skilled in the art can select the one most suitable for a particular feed and catalyst.

With the use of liquid catalysts, such as hydrofluoric acid (with and without boron trifluoride) and sulfuric acid, the contact time of the hydrocarbon feedstock with the catalyst is preferably in the range of from about 5 seconds to about 1 hour; more preferably from about 10 seconds to about 30 minutes; and most preferably from 30 seconds to 30 minutes.

With the use of a solid catalyst, such as, but not limited to, polyfluoroalkyl sulfonic acids; perfluoroalkyl sulfonic acids; zeolites; alumina; aluminosilicates; and zirconia-based solid acids, the flow rate at which the hydrocarbon feedstock is charged to the disproportionation reactor is such as to provide a weight hourly space velocity ("WHSV", defined as the pounds/hour of feed to the reaction zone divided by the total pounds of catalyst contained within the reaction zone) in the range of from about 0.01 hours to about 1000 $hr^{-1}$; preferably from about 0.25 $hour^{-1}$ to about 250 $hour^{-1}$ and most preferably from 0.5 $hour^{-1}$ to 100 $hour^{-1}$.

The reaction temperature can be in the range of from about 50° F. to about 200° F.; preferably from about 90° F. to about 180° F.; and most preferably from 110° F. to 160° F. The pressure of the reactor can be in the range of from about 50 psig to about 1000 psig; preferably from about 75 psig to about 500 psig; and most preferably from 100 psig to 250 psig.

The product stream from the disproportionation reactor comprises isoparaffins and paraffins having the formulas $C_{n-1}H_{2n}$, and $C_{n+1}H_{2n+4}$ (which are disproportionation products of a hydrocarbon having the formula $C_nH_{2n+2}$). The isoparaffins and paraffins of the product stream, resulting from the disproportionation, are generally less isomerized than the isoparaffins of the hydrocarbon feedstock. The terms "isomerized" and "isomer", as used herein, are defined as the degree of branching of a molecule. For instance, per this definition, 2,4 dimethylpentane:

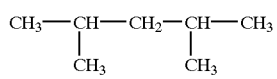

is more highly branched, and thus more isomerized, than 2 methylhexane:

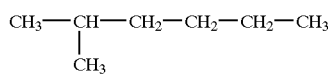

which is more highly branched, and thus more isomerized, than heptane:

while each of these contain the exact same number of carbon and hydrogen atoms.

More particularly, the product stream comprises a diesel range material comprising at least one hydrocarbon having greater than 8 carbon atoms per molecule and a gasoline range material comprising at least one hydrocarbon having less than 9 carbon atoms per molecule.

The combined volume of the gasoline range material produced and the diesel range material produced is preferably greater than the volume of the hydrocarbon feedstock.

The product stream can be separated into the diesel range material and the gasoline range material by any method known for separating hydrocarbons, such as a distillation unit.

The diesel range material has a cetane number, as determined using ASTM test method D613.65, which is higher than the cetane number of the hydrocarbon feedstock. The cetane number of the hydrocarbon feedstock is typically less than 25, more typically less than 24, and most typically less than 23. Preferably, the product diesel range material has a cetane number greater than about 25; more preferably greater than about 28; and most preferably greater than 30.

The product gasoline range material preferably has in the range of from 5 to 8 carbon atoms per molecule. The octane rating of the product gasoline range material is preferably higher than the octane-rating of the hydrocarbon feedstock.

Octane-rating is defined as (RON+MON)/2. RON (research octane number), as used herein, refers to the octane number of a hydrocarbon stream as determined using the ASTM D-2699 method. MON (motor octane number), as used herein, refers to the octane number of a hydrocarbon stream as determined using the ASTM D-2700 method.

The octane-rating of the hydrocarbon feedstock is typically less than about 78, more typically less than about 76, and most typically less than 74. Preferably, the octane-rating of the product gasoline range material is greater than about 78; more preferably greater than about 79; and most preferably greater than 80.

In another embodiment, an i-$C_5$ stream comprising isopentane can be recovered from the product stream before separation of the product stream into the gasoline range material and diesel range material; or from the gasoline range material after separation of the gasoline range material and diesel range material from the product stream. The recovered i-$C_5$ stream can be contacted with the disproportionation catalyst in the disproportionation reactor along with the hydrocarbon feedstock. This leads to the production of more isobutane, an alkylation unit feedstock; more $C_6$ hydrocarbons, a desirable gasoline component; and a lower level of produced isopentane, which is desirable due to the relatively high RVP (reid vapor pressure) of isopentane and gasoline specifications which limit the level of RVP.

The following example is presented to further illustrate the invention and is not be be construed as unduly limiting its scope.

EXAMPLE

This example illustrates the inventive process of disproportionating a hydrocarbon feedstock comprising isoparaffins and paraffins to produce a product stream comprising a gasoline range material having the benefit of a higher octane-rating than the hydrocarbon feedstock and a diesel range material having the benefit of a higher cetane number than the hydrocarbon feedstock.

A 736.13 gram quantity of heavy alkylate from a refinery alkylation unit was blended with 13.0 grams of 2-methylbutene-2 to produce a constant hydrocarbon feed for the following Runs 1–7.

In Run 1, a 100 gram quantity of a 99 wt. % HF/1 wt. % water mixture was placed in an autoclave reactor including a stirring shaft and impeller. Air present in the autoclave reactor was evacuated and $N_2$ gas was added to a pressure of 200 psig. At this time, 100 mL of the hydrocarbon feed was introduced to the autoclave reactor with a stirring rate of 1000 rpm. The reactor contents were initially heated to a temperature of about 117° F. and the autoclave reactor pressure was maintained at 200 psig. The reactor temperature, after 30 minutes of contact time, was about 113.1° F. The product was collected for analysis after 30 minutes of contact time and analysis was by means of a gas chromatograph. Test data results are summarized in the Table.

In Run 2, the autoclave reactor and HF/water mixture from Run 1 were utilized. $N_2$ gas was added to a pressure of 200 psig. At this time, 100 mL of the hydrocarbon feed was introduced to the autoclave reactor with a stirring rate of 1000 rpm. The reactor contents were initially heated to a temperature of about 127.6° F. and the autoclave reactor pressure was maintained at 200 psig. The reactor temperature, after 30 minutes of contact time, was about 138.3° F. The product was collected for analysis after 30 minutes of contact time and analysis was by means of a gas chromatograph. Test data results are summarized in the Table.

In Run 3, the autoclave reactor and HF/water mixture from Run 2 were utilized. $N_2$ gas was added to a pressure of 200 psig. At this time, 100 mL of the hydrocarbon feed was introduced to the autoclave reactor with a stirring rate of 1000 rpm. The reactor contents were initially heated to a temperature of about 152.9° F. and the autoclave reactor pressure was maintained at 200 psig. The reactor temperature, after 30 minutes of contact time, was about 145.7° F. The product was collected for analysis after 30 minutes of contact time and analysis was by means of a gas chromatograph. Test data results are summarized in the Table.

Two more runs (4 and 5) were made, similar to Run 3, but with low conversion due to deactivation of the HF/water catalyst. At this time, 33.84 grams of the HF/water mixture in the autoclave reactor were removed and 71.01 grams of HF were added to the autoclave reactor.

In Run 6, the autoclave reactor and HF/water mixture, prepared as above described, were utilized. $N_2$ gas was added to a pressure of 200 psig. At this time, 100 mL of the hydrocarbon feed was introduced to the autoclave reactor with a stirring rate of 1000 rpm. The reactor contents were initially heated to a temperature of about 142.5° F. and the autoclave reactor pressure was maintained at 200 psig. The reactor temperature, after 30 minutes of contact time, was about 144.7° F. The product was collected for analysis after 30 minutes of contact time and analysis was by means of a gas chromatograph. Test data results are summarized in the Table.

In Run 7, the autoclave reactor and HF/water mixture from Run 6 were utilized. $N_2$ gas was added to a pressure of 200 psig. At this time, 100 mL of the hydrocarbon feed was introduced to the autoclave reactor with a stirring rate of 1000 rpm. The reactor contents were initially heated to a temperature of about 147.5° F. and the autoclave reactor pressure was maintained at 200 psig. The reactor temperature, after 30 minutes of contact time, was about 143.8° F. The product was collected for analysis after 30 minutes of contact time and analysis was by means of a gas chromatograph. Test data results are summarized in the Table.

The products of Runs 1, 2, 3, 6 and 7 were combined. The $C_8$ and lighter components were allowed to evaporate off to the point where the concentration of $C_6$–$C_8$ components in the product was in the range of the concentration of $C_6$–$C_8$ components present in the hydrocarbon feed (1.75 wt. % $C_6$–$C_8$ in the product as compared to 2.16 wt. % $C_6$–$C_8$ in the feed). Having approximately equal $C_6$–$C_8$ component weight percents in the feed and product allowed a proper comparison of the cetane numbers of the feed and product, as measured by the following method.

The cetane of the hydrocarbon feed (heavy alkylate without added 2-methylbutene-2, "2-MB-2") was determined as follows.

A mixture was prepared comprising:

20 volume % hydrocarbon feed; and 80 volume % diesel fuel having a cetane number of 41.3.

The cetane of the mixture was determined using ASTM test method D613.65 and was 37.4. The cetane of the hydrocarbon feed was calculated as follows:

$$\left(\frac{20 \text{ vol. \% hydrocarbonfeed}}{100}\right) * X + \left(\frac{80 \text{ vol. \% diesel fuel}}{100}\right) * 41.3 = 37.4$$

X=calculated cetane of the hydrocarbon feed=21.8.

The cetane of the $C_9$+ product was determined as follows.

A mixture was prepared comprising:

19.2 volume % $C_9$+ product; and 80.8 volume % diesel fuel having a cetane number of 41.3.

The cetane of the mixture was determined using ASTM test method D613.65 and was 39.7. The cetane of the $C_9$+ product was calculated as follows:

$$\left(\frac{19.2 \text{ vol. \% } C_9 + \text{product}}{100}\right) * X + \left(\frac{80.8 \text{ vol. \% diesel fuel}}{100}\right) * 41.3 = 39.7$$

X=calculated cetane of the $C_9$+ product=33.0.

TABLE

| | | Run 1 | | | Run 2 | | | Run 3 | | | Run 6 | | | Run 7 | | |
|---|---|---|---|---|---|---|---|---|---|---|---|---|---|---|---|---|
| Component | Feed wt. % | $C_5$–$C_8$[1] Product | $C_9$+[2] Product | $C_4$– Product | $C_5$–$C_8$[1] Product | $C_9$+[2] Product | $C_4$– Product | $C_5$–$C_8$[1] Product | $C_9$+[2] Product | $C_4$– Product | $C_5$–$C_8$[1] Product | $C_9$+[2] Product | $C_4$– Product | $C_5$–$C_8$[1] Product | $C_9$+[2] Product | $C_4$– Product |
| $iC_4$ & lighter | — | — | — | 6.04 | — | — | 6.53 | — | — | 6.37 | — | — | 5.97 | — | — | 4.86 |
| $iC_5$= (2MB1 + 2MB2) | 1.82 | — | — | — | — | — | — | — | — | — | — | — | — | — | — | — |
| $iC_5$ | 0 | 6.86 | — | — | 7.35 | — | — | 6.89 | — | — | 7.00 | — | — | 5.53 | — | — |

TABLE-continued

| Component | Feed wt. % | Run 1 $C_5$–$C_8^1$ Product | Run 1 $C_9+^2$ Product | Run 1 $C_4$– Product | Run 2 $C_5$–$C_8^1$ Product | Run 2 $C_9+^2$ Product | Run 2 $C_4$– Product | Run 3 $C_5$–$C_8^1$ Product | Run 3 $C_9+^2$ Product | Run 3 $C_4$– Product | Run 6 $C_5$–$C_8^1$ Product | Run 6 $C_9+^2$ Product | Run 6 $C_4$– Product | Run 7 $C_5$–$C_8^1$ Product | Run 7 $C_9+^2$ Product | Run 7 $C_4$– Product |
|---|---|---|---|---|---|---|---|---|---|---|---|---|---|---|---|---|
| $C_6$–$C_8$ | 2.17 | 19.82 | — | — | 20.34 | — | — | 19.15 | — | — | 20.16 | — | — | 16.28 | — | — |
| $C_9+$ | 96.01 | — | 67.22 | — | — | 65.78 | — | — | 67.60 | — | — | 66.87 | — | — | — | — |
| Total wt. % | 100.0 | 26.68 | 67.22 | 6.04 | 27.69 | 65.78 | 6.53 | 26.03 | 67.60 | 6.37 | 27.16 | 66.87 | 5.97 | 21.81 | — | 4.86 |
| RON | $68.5^3$ | $78.5^4$ | — | — | $78.6^4$ | — | — | $79.2^4$ | — | — | $78.8^4$ | — | — | $79.5^4$ | — | — |
| MON | $77.5^3$ | $77.4^4$ | — | — | $77.5^4$ | — | — | $77.9^4$ | — | — | $77.6^4$ | — | — | $78.2^4$ | — | — |
| Octane-rating$^5$ | 73.0 | 78.0 | — | — | $78.0^5$ | — | — | $78.6^5$ | — | — | $78.2^5$ | — | — | $78.8^5$ | — | — |
| cetane | $21.8^7$ | — | $33^8$ | — | — | $33^8$ | — | — | $33^8$ | — | — | $33^8$ | — | — | $33^8$ | — |
| Volume$^6$ (mL) | 100 | 30.1 | 67.6 | 8.1 | 31.7 | 66.4 | 8.6 | 29.8 | 68.0 | 8.3 | 31.1 | 67.3 | 7.8 | 24.9 | 73.8 | 6.37 |
| Total Volume$^4$ (mL) | 100 | | 105.8 | | | 106.7 | | | 106.1 | | | 106.2 | | | 105.1 | |

$^1$gasoline range material;
$^2$diesel range material;
$^3$measured values using ASTM test methods D-2699 and D-2700 of heavy alkylate in feed without added $iC_5$=;
$^4$estimated values based on known values for pure components;
$^5$(RON + MON)/2;
$^6$based on 100 mL feed;
$^7$measured value of heavy alkylate in feed without added $iC_5$=;
$^8$measured cetane of the combination of the $C_9+$ product's for Runs 1, 2, 3, 6, 7.

The test data presented in the Table show that the disproportionation of a hydrocarbon feedstock comprising isoparaffins and paraffins (heavy alkylate) produces a product comprising a gasoline range material having a higher octane-rating than the hydrocarbon feedstock, a diesel range material having a higher cetane number than the hydrocarbon feedstock, and a total volume of gasoline and diesel range materials which is higher than the hydrocarbon feedstock volume.

The octane-ratings of the gasoline range material in Runs 1,2,3,6, and 7 ranged from 5.0 to 5.8 numbers higher than the octane-rating of the hydrocarbon feedstock.

The cetane number of the diesel range material (Runs 1,2,3,6, and 7 combined) is 11 numbers higher than the cetane number of the hydrocarbon feedstock.

Also, the total volumes of the products in Runs 1,2,3,6, and 7 ranged from 5.1% to 6.7% higher than the volume of the hydrocarbon feedstock.

Reasonable variations, modifications, and adaptations can be made within the scope of the disclosure and the appended claims without departing from the scope of this invention.

That which is claimed is:

1. A process for disproportionating hydrocarbons comprising:

contacting a hydrocarbon feedstock comprising isoparaffins and paraffins with a disproportionation catalyst selected from the group consisting of hydrofluoric acid, sulfuric acid, polyfluoroalkylsulfonic acid, perfluoroalkylsulfonic acid, zirconia-based solid acids, and combinations of any two or more thereof, in the presence of at least one initiator selected from the group consisting of ethylene, at least one compound of the formula $C_nH_{2n+1}X$, wherein n is an integer and wherein X is a leaving group capable of leaving under disproportionation conditions to form a carbocation intermediate, and combinations of any two or more thereof, to thereby produce a product stream comprising a diesel range material; and recovering said diesel range material from said product stream.

2. A process in accordance with claim 1 wherein said disproportionation catalyst consists essentially of hydrofluoric acid.

3. A process in accordance with claim 1 wherein said disproportionation catalyst comprises sulfuric acid.

4. A process in accordance with claim 2 wherein said diesel range material has a cetane number which is higher than the cetane number of said hydrocarbon feedstock.

5. A process in accordance with claim 2 further characterized to include a weight ratio, of said hydrocarbon feedstock to said at least one initiator, in the range of from about 1:1 to about 100,000:1.

6. A process in accordance with claim 2 further characterized to include a weight ratio, of said hydrocarbon feedstock to said at least one initiator, in the range of from about 10:1 to about 1,000:1.

7. A process in accordance with claim 2 further characterized to include a weight ratio, of said hydrocarbon feedstock to said at least one initiator, in the range of from 20:1 to 100:1.

8. A process in accordance with claim 2 wherein said diesel range material has a cetane number greater than about 25.

9. A process in accordance with claim 2 wherein said diesel range material has a cetane number greater than about 28.

10. A process in accordance with claim 2 wherein said diesel range material has a cetane number greater than 30.

11. A process in accordance with claim 2 wherein said contacting of said hydrocarbon feedstock with said disproportionation catalyst is for a time period in the range of from about 5 seconds to about 1 hour.

12. A process in accordance with claim 2 wherein said contacting of said hydrocarbon feedstock with said disproportionation catalyst is at a temperature in the range of from about 50° F. to about 200° F.

13. A process in accordance with claim 2 wherein said initiator comprises at least one compound of the formula $C_nH_{2n+1}X$, wherein n is an integer and wherein X is a leaving group capable of leaving under disproportionation conditions to form a carbocation intermediate.

14. A process in accordance with claim 13 wherein X is a leaving group selected from the group consisting of fluorine, chlorine, bromine, iodine, hydroxide ion, and combinations of any two or more thereof.

15. A process in accordance with claim 2 wherein X is a leaving group selected form the group consisting of fluorine, chlorine, bromine, iodine, hydroxide ion, and combinations of any two or more thereof.

16. A process in accordance with claim 2 wherein said diesel range material is characterized further to include hydrocarbons having greater than 8 carbon atoms per molecule.

17. A process for converting at least a portion of a hydrocarbon feedstock comprising isoparaffins and paraffins to a gasoline range material and a diesel range material, said process comprising:

contacting said hydrocarbon feedstock with a catalyst system consisting essentially of 1) a disproportionation catalyst selected from the group consisting of sulfuric acid, polyfluoroalkylsulfonic acid, perfluoroalkylsulfonic acid, zirconia-based solid acids, and combinations of any two or more thereof, and 2) at least one initiator selected from the group consisting of at least one olefin, at least one compound of the formula $C_nH_{2n+1}X$, wherein n is an integer and wherein X is a leaving group capable of leaving under disproportionation conditions to form a carbocation intermediate, and combinations of any two or more thereof, to thereby produce said gasoline range material and said diesel range material.

18. A process in accordance with claim 17 further characterized to include the steps of:

recovering an i-$C_5$ stream comprising isopentane from said gasoline range material; and contacting said i-$C_5$ stream with said disproportionation catalyst along with said hydrocarbon feedstock.

19. A process in accordance with claim 17 wherein said isoparaffins and said paraffins comprise hydrocarbons having greater than 8 carbon atoms per molecule.

20. A process in accordance with claim 17 wherein said diesel range material has a cetane number greater than about 25.

21. A process in accordance with claim 17 wherein said diesel range material has a cetane number greater than about 28.

22. A process in accordance with claim 17 wherein said diesel range material has a cetane number greater than about 30.

23. A process in accordance with claim 17 wherein said initiator comprises at least one compound of the formula $C_nH_{2n+1}X$, wherein n is an integer and wherein X is a leaving group capable of leaving under disproportionation conditions to form a carbocation intermediate.

24. A process in accordance with claim 23 wherein X is a leaving group selected from the group consisting of fluorine, chlorine, bromine, iodine, hydroxide ion, and combinations of any two or more thereof.

25. A process in accordance with claim 17 wherein X is a leaving group selected form the group consisting of fluorine, chlorine, bromine, iodine, hydroxide ion, and combinations of any two or more thereof.

26. A process in accordance with claim 17 wherein said gasoline range material is characterized further to comprise hydrocarbons having in the range of from 5 to 8 carbon atoms per molecule and said diesel range material is characterized further to comprise hydrocarbons having greater than 8 carbon atoms per molecule.

27. A process in accordance with claim 17 wherein said disproportionation catalyst is sulfuric acid.

28. A process for converting at least a portion of a hydrocarbon feedstock consisting essentially of isoparaffins of the formula $C_nH_{2n+2}$, wherein n in said formula $C_nH_{2n+2}$ is an integer greater than 8, said process comprising:

contacting said hydrocarbon feedstock with a disproportionation catalyst selected from the group consisting of hydrofluoric acid, sulfuric acid, polyfluoroalkylsulfonic acid, perfluoroalkylsulfonic acid, zirconia-based solid acids, and combinations of any two or more thereof, in the presence of at least one initiator selected from the group consisting of ethylene, at least one compound of the formula $C_nH_{2n+1}X$, wherein n in said formula $C_nH_{2n+1}X$ is an integer and wherein X is a leaving group capable of leaving under disproportionation conditions to form a carbocation intermediate, and combinations of any two or more thereof, to thereby produce a product stream comprising hydrocarbons having the formulas of $C_nH_{2n}$ and $C_{n+1}H_{2n+4}$, wherein n in said formula $C_{n-1}H_{2n}$ is an integer, wherein n in said formula $C_{n+1}H_{2n+4}$ is an integer.

29. A process in accordance with claim 28 further characterized to include the step of:

separating said product stream into a gasoline range material comprising at least one hydrocarbon having less than 9 carbon atoms per molecule and a diesel range material comprising at least one hydrocarbon having more than 8 carbon atoms per molecule.

30. A process in accordance with claim 29 further characterized to include the steps of:

recovering an i-$C_5$ stream comprising isopentane from said gasoline range material; and contacting said i-$C_5$ stream with said disproportionation catalyst along with said hydrocarbon feedstock.

31. A process in accordance with claim 29 wherein said diesel range material has a higher cetane number than said hydrocarbon feedstock.

32. A process in accordance with claim 29 wherein said diesel range material has a cetane number greater than about 25.

33. A process in accordance with claim 29 wherein said diesel range material has a cetane number greater than about 28.

34. A process in accordance with claim 29 wherein said diesel range material has a cetane number greater than 30.

35. A process in accordance with claim 29 wherein said gasoline range material has a higher octane-rating than said hydrocarbon feedstock.

36. A process in accordance with claim 29 wherein said gasoline range material has an octane-rating greater than about 78.

37. A process in accordance with claim 29 wherein said gasoline range material has an octane-rating greater than about 79.

38. A process in accordance with claim 29 wherein said gasoline range material has an octane-rating greater than 80.

39. A process in accordance with claim 28 wherein said contacting of said hydrocarbon feedstock with said disproportionation catalyst is for a time period in the range of from about 5 seconds to about 1 hour.

40. A process in accordance with claim 28 wherein said contacting of said hydrocarbon feedstock with said disproportionation catalyst is at a temperature in the range of from about 50° F. to about 200° F.

41. A process in accordance with claim 28 wherein said initiator comprises at least one compound of the formula $C_nH_{2n+1}X$, wherein n is an integer and wherein X is a leaving group capable of leaving under disproportionation conditions to form a carbocation intermediate.

42. A process in accordance with claim 41 wherein X is a leaving group selected from the group consisting of fluorine, chlorine, bromine, iodine, hydroxide ion, and combinations of any two or more thereof.

* * * * *